United States Patent [19]

Tsav

[11] Patent Number: 5,110,910

[45] Date of Patent: May 5, 1992

[54] VIRUCIDAL EUGLOBULIN PRECIPITATION

[75] Inventor: Grace C. Tsav, Walnut Creek, Calif.

[73] Assignee: Miles Inc., Elkhart, Ind.

[21] Appl. No.: 673,991

[22] Filed: Mar. 25, 1991

[51] Int. Cl.$^5$ .................... A61K 39/395; C07K 3/24
[52] U.S. Cl. ................ 530/390.1; 424/85.8; 530/418; 530/863; 530/831
[58] Field of Search ............... 530/387, 418; 424/85.8

[56] References Cited

U.S. PATENT DOCUMENTS

| | | | |
|---|---|---|---|
| 4,165,370 | 8/1979 | Coval | 424/85.8 |
| 4,540,573 | 9/1985 | Neurath et al. | 530/387 |

OTHER PUBLICATIONS

Steinbuch et al., (1973) Prep. Biochem. 3(4):363-373.

*Primary Examiner*—Robert A. Wax
*Assistant Examiner*—Richard C. Ekstrom
*Attorney, Agent, or Firm*—James A. Giblin

[57] ABSTRACT

A source for antibodies (both IgG and IgM types) is put into an aqueous solution which includes a virucidal agent under conditions sufficient to assure substantially complete dissolution of both the antibodies and the virucidal agent and virus inactivation. Then the pH, conductivity and antibody concentration of the solution are then changed to obtain conditions sufficient to assure the precipitation of substantially all antibodies while maintaining substantially all of the virucidal agent in the supernatant solution.

In preferred embodiments, using a TNBP/TWEEN virucidal agent, the original solution conductivity ranges from about 0.03 to 0.20 M MHO/CM, the pH ranges from about 4.75 to 4.85, and the protein concentration, when measured at A280, ranges from a reading of about 5 to 40. In the second precipitation step, the pH is changed to a range of about 6.0 to 7.5 and the conductivity is changed to a range of about 0.05 to 0.70 M MHO/CM to achieve an IgM precipitation ranging from about 30 to 80% by weight total protein.

7 Claims, 2 Drawing Sheets

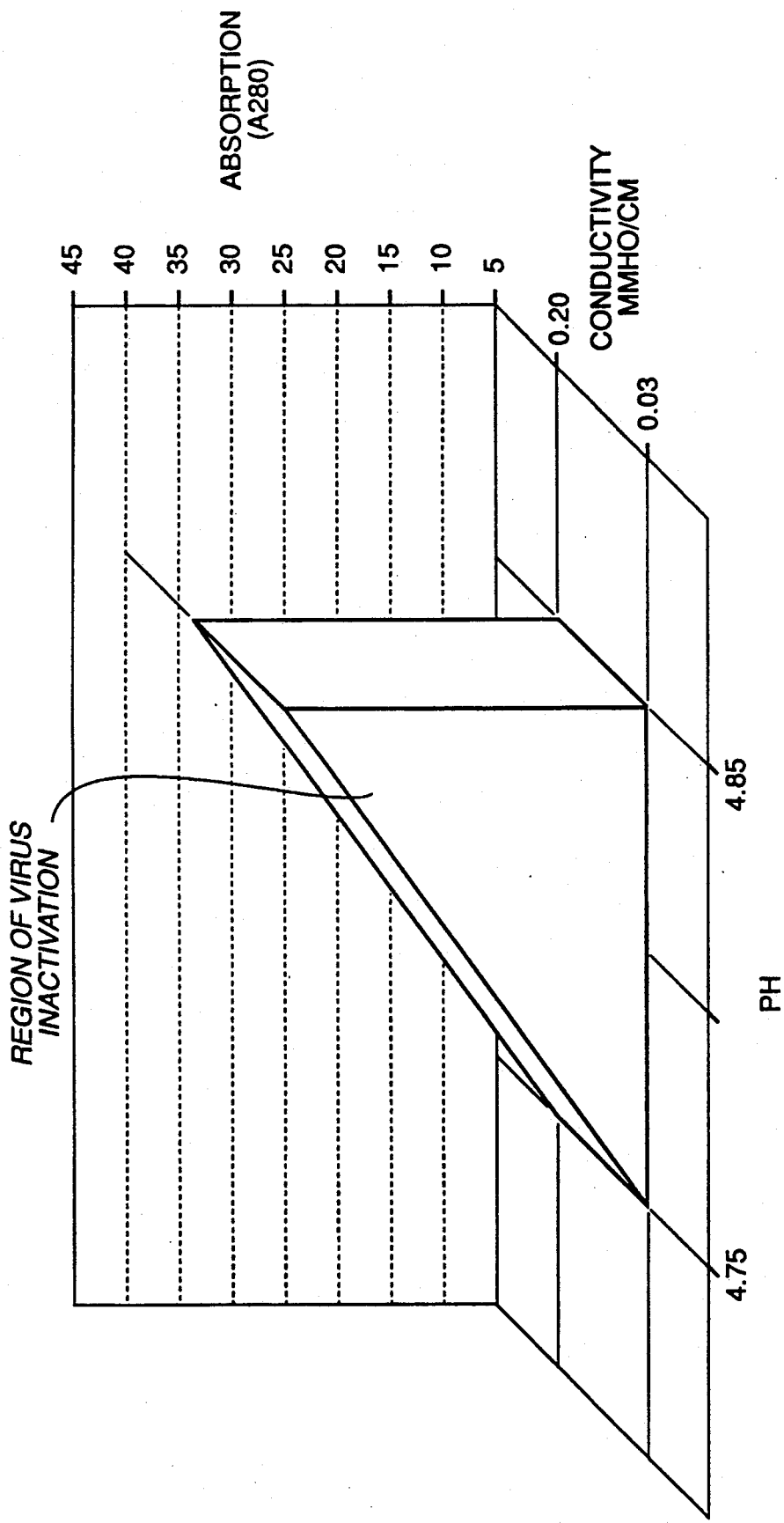
FIG._1

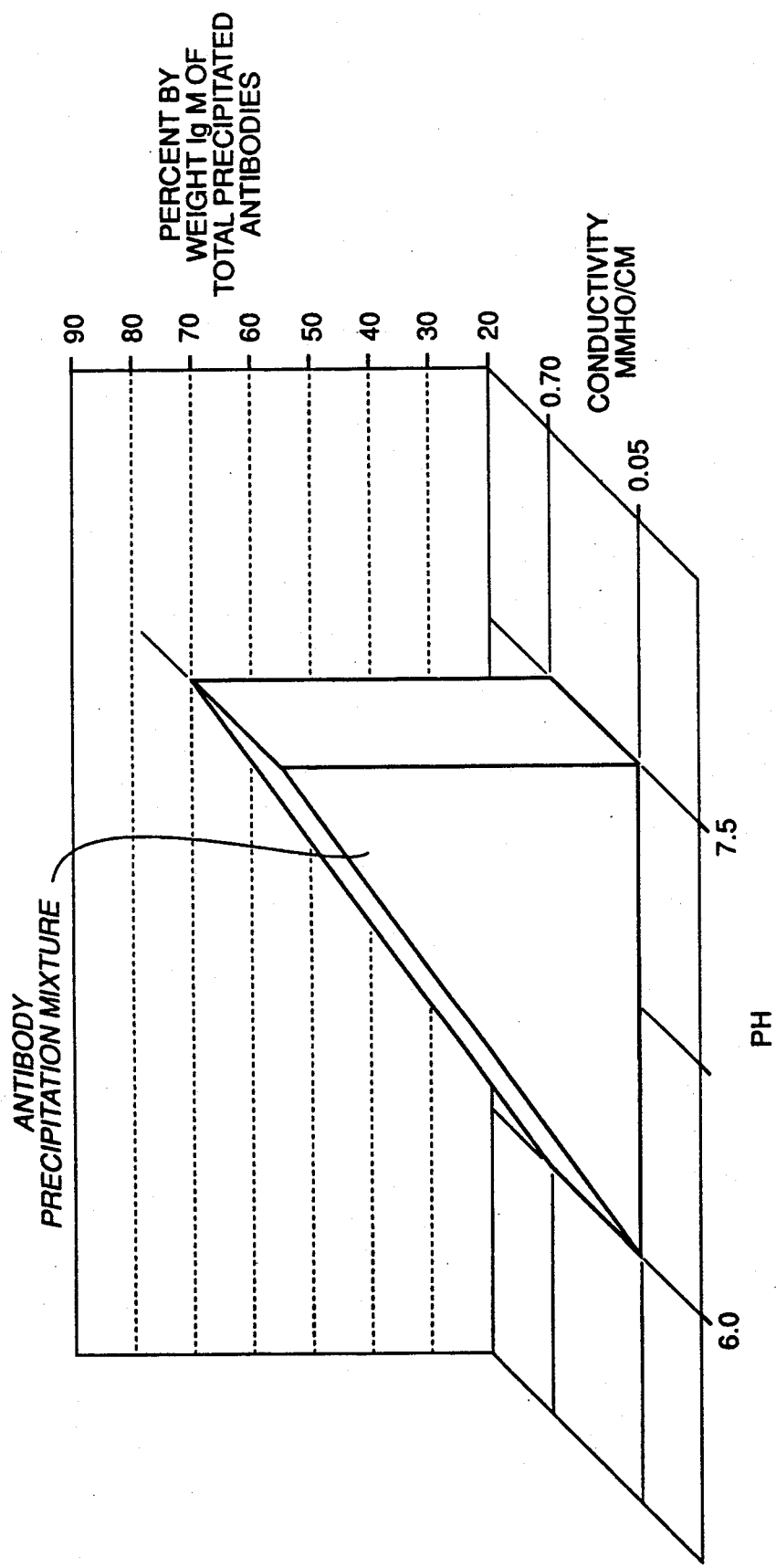
FIG._2

VIRUCIDAL EUGLOBULIN PRECIPITATION

BACKGROUND OF THE INVENTION

1. Field:

This disclosure is concerned generally with the preparation of antibodies and specifically with the use of a virucidal agent in a process for precipitating antibodies from an antibody source that may include dangerous viruses.

2. Prior Art:

Antibodies are high molecular weight proteins that can be obtained from blood or more recently, from cultures of single cell lines (clones) that express monoclonal antibodies. The antibodies obtained from blood are commonly made by fractionating blood plasma using any of several processes such as one of the processes known as the Cohn process or a variation of it.

Antibodies are often classified as to type (IgG, IgM, IgA, etc.) and sometimes as to sub-type (IgG1, IgG2, IgG3, and IgG4). When obtained from plasma for therapeutic purposes, most antibodies prepared are of the IgG type (e.g. Gamimune ®, available from Miles Inc.; Gamagard ™, available from Baxter International; Sandimune ™, available from Sandoz; and Venoglobulin ™, from Alpha Therapeutics. Although therapeutic IgM products are not common, at least one product comprising IgM enriched IgG is available in Europe from Biotest, Gmbh (Pentaglobin ™). It is believed the preparation of this product is described generally in U.S. Pat. No. 4,318,902, to Stephan.

More recently, the preparation of IgM—including therapeutic products has been described in U.S. patent application Ser. No. 83,136 in the name of G. Dove et al (primarily monoclonal IgM antibodies) and U.S. patent application Ser. No. 203,377 in the name of M.S. Collins et al (primarily plasma-derived IgM). See also patent application Ser. No. 504,161 in the name of G. C. Tsay et al (heat treated IgM preparations).

In preparing IgM enriched antibodies, it should be noted that there exists a potential, however remote, for the presence of viruses. While the source of such viruses can be either blood plasma or a monoclonal antibody cell culture, the potential for viral contamination is of special concern when the antibodies are derived from plasma using what is known as Cohn Fraction III. Fraction III, because of the processing steps that precede its generation, is a potential repository of blood-borne viruses that must be inactivated or removed for safety of a therapeutic IgM containing product.

While it is well known that IgG and IgM enriched products can be obtained (purified) from an aqueous solution by a process known as globulin or euglobulin precipitation, very little studies or prior art exist on assuring the inactivation of viruses in this process. Against this background, I have discovered a novel process for preparing an IgM-enriched IgG product that permits a relatively high IgM recovery while permitting a simultaneous viral inactivation step. Details of my process are described below.

SUMMARY OF INVENTION

Method of preparing an antibody preparation comprising antibodies of the IgM and IgG types comprising two steps. In the first step, a source for the antibodies is put into an aqueous solution which includes a virucidal agent under conditions sufficient to assure substantially complete dissolution of both the antibodies and the virucidal agent and virus inactivation. In the second step, the pH, conductivity and antibody concentration of the solution are changed under conditions sufficient to assure the precipitation of substantially all antibodies while maintaining substantially all of the virucidal agent in the supernatant solution. In preferred embodiments, using a TNBP/TWEEN virucidal agent, the original solution conductivity ranges from about 0.03 to 0.20 M MHO/CM, the pH ranges from about 4.75 to 4.85, and the protein concentration, when measured at A280, ranges from a reading of about 5 to 40. In the second precipitation step, the pH is changed to a range of about 6.0 to 7.5 and the conductivity is changed to a range of about 0.05 to 0.70 M MHO/CM to achieve an IgM precipitation ranging from about 30 to 80% by weight total protein.

BRIEF DESCRIPTION OF THE FIGURES

FIG. 1 (step 1) is a three dimensional graph showing parameters of pH, conductivity and protein concentration at A280 found useful for assuring that all antibodies remain in solution during the viral inactivation process when using a specific virucidal agent.

FIG. 2 (step 2) is a three dimensional graph showing parameters of pH and conductivity to which the solution represented by the graph of FIG. 1 must be changed to assure a given IgM recovery while retaining the virucidal agent in solution.

SPECIFIC EMBODIMENTS

As noted above, the process of this disclosure consists of two general steps, a solution/viral inactivation step followed by a solution/precipitation step in which substantially all (at least 40%) of the IgM (which is 30 to 80% by weight of total protein) precipitates out of solution while substantially all (i.e., at least 99.9% by weight) of the virucidal agent remains in the supernate solution. In my examples, I found that the pH, conductivity (ionic strength) and protein concentration are critical, depending on the needs of the step.

In the first step, the pH must be about 4.75 to 4.85. If lower than 4.75, viral inactivation still takes place but the subsequent precipitate will result in a lower antibody yield. If the pH is above 4.85, there is less virus inactivation, especially at lower solution conductivity.

The conductivity of the solution of the first step, measured in MMHO/CM, should be from about 0.03 to 0.20. If below 0.03, protein will precipitate out while still in step 1. If above 0.20, the protein will not precipitate out as required in step 2. Also, as the salt concentration/ conductivity increase, there is less chance that the protein of step 2 will precipitate in a manner that isolates it from the virucidal agent in the supernate.

The total protein concentration of the step 1 solution, as measured by absorbance at a wave length of 280mu (A280), should range from about 5 to 40. If below 5, the concentration of the protein is too low to result in a good precipitate in step 2. If above 40, the virucide may not be effective in that, possibly, the protein may tend to protect the virus from the virucidal agent's actions.

The overall relationship of the above ranges for step 1 are illustrated in the graph of FIG. 1.

A significant part of the invention of this disclosure occurs in the precipitation step 2. In that step, the pH and conductivity of step 1 must be changed to assure precipitation of substantially all antibodies while retaining substantially all virucidal agent in the supernate.

The pH must be increased from about 6.0 to 7.5. Below 6.0, there will be no significant antibody precipitation. Above 7.5, there will also be no significant precipitation as the protein will be forced back into solution. It is significant to note that the relative proportion of IgM to IgG recovered during this step is related directly to the precise pH chosen within that range. Also, it should be understood that the virucidal agent must be water soluble throughout the above pH range and the conductivity range (below) to assure a clean separation in the supernate.

The step 2 conductivity ranges from 0.05 to 0.70 MMHO/CM. The lower range (~0.05) is assured using, for example, NaOH while the conductivity can be increased toward the upper and of the range (0.70) using, for example, tris buffer. If the conductivity is below 0.05 or above 0.70, the antibody yield is lower and the proportion of IgM to IgG drops to an undesirable level.

FIG. 2 graphically shows how the control of the step 2 parameter of pH and conductivity can be related in step to assure obtaining substantially all of the 30% to 80% by weight of IgM in an IgM/IgG mixture. Although the IgM ranges from 30% to 80% on a wt/wt basis and antibody source, it will be appreciated that some IgA (<20% by wt.) may be present if the antibody source is Cohn Fraction III.

It is thought that a wide variety of virucidal agents may be used alone or with detergents (such as Tween) to accomplish the goals of both step 1 and step 2. For step 1, the agent must be present under conditions sufficient to assure substantial inactivation of all viruses. This can be determined readily. The virucidal agent must also be very water soluble for step 1 and especially in the changed environment of step 2.

In the examples below, I used tri-n-butyl-phosphate (TNBP) as a virucidal agent and TWEEN as a detergent. This is a preferred viral inactivation system and the use of TNBP in biological products is described in detail in U.S. Pat. No. 4,540,573, to Horowitz et al. Other suitable virucidal agents include unsaturated fatty acid, $\beta$-propiolactone, 1, 10-phenanthroline cuprous ion complex, caprylic acid and ethylene glycol.

Details of one of the very preferred processes of this invention are given below for an IgM/IgG concentrate made from Cohn Fraction III.

The plasma-derived IgM, IgG immunoglobulin concentrates prepared from Cohn fraction III may contain virus contamination. Virus inactivation has been demonstrated in the caprylate supernatant after DF/UF adjusted pH to 4.8 and treated with 0.3% TNBP/1% Tween-80. If TNBP/Tween is removed via the diafiltration system, the TNBP may cause diafiltration membrane system damage and tween with protein solution formed miscellanea could not be removed by the diafiltration system. The TNBP/Tween removal also has been achieved by euglobulin precipitation with 0.01 M tris pH 7.8 and resulted in less than 0.4 $\mu$g TNBP/Tween per mg IgM in the final IgM, IgG immunoglobulin concentration.

INTRODUCTION

Employing caprylic acid to precipitate most proteins other than the immunoglobulins and following euglobulin precipitation, the enriched immunoglobulin M with low ionic strength buffer system was made to prepare enriched immunoglobulin M from Cohn fraction III of pooled normal plasma. Different buffer systems such as tris, imidazole, phosphate, carbonate at different pH, concentration, and temperature were applied to study their effects on IgM, IgG, IgA precipitation. The low conductivity (<0.05 mmho/cm) and pH 4.8 in the caprylate supernatant prepared from Cohn fraction III paste were virus inactivated with tri-n-butyl)phosphate (TNBP)/Tween mixtures and carried out for euglobulin precipitation.

TNBP/Tween removal has been demonstrated to reach acceptable traces in the IgM, IgG immunoglobulin concentrates by euglobulin precipitation. The virus inactivated IgM, IgG immunoglobulin concentrates are candidates for further mild heat treatment to increase product safety margin for human clinical use.

IgM, IgG immunoglobulin concentrates were prepared from Cohn fraction III of pooled normal plasma by multiple methods such as polyethylene glycol precipitation (Wickerhauser M, and Hao YL; Large scale preparation of macroglobulins. Vox Sang 1972;23:119–125 and Van Der Hoven A, Conradie JD, Bubb M: The isolation of immunogenically pure IgM from Cohn fraction III of pooled normal human plasma, Immunochemistry 1973;10:107–114); ethanol precipitation at pH 6.0 (Steinbuch M, Andran R, Pejaudier L, et al; Preparation of an IgM and IgA enriched fraction for clinical use, Preparative Biochemistry 1973;3(4):363–373); euglobulin precipitation by dialysis against 0.001 M phosphate buffer pH 6.5 (Van Der Hoven A, et al, ibid.); affinity chromatography on protamine-Sepharose (Wichman A, Borg H; Purification of human immunoglobulin M by affinity chromatography on protamine-sepharose; Biochim Biophys Acta 1977;490:363–369); and $\beta$-propiolactone treatment of concentrated immunoglobulin M solution suitable for intravenous administration (Stephan W; Hepatitis free and stable human serum for intravenous therapy, Vox Sang 1971;20:442–457 and Stephan W; Concentrated immunoglobulin solution suited for intravenous administration, U.S. Pat. No. 4,318,902, Mar. 9, 1982).

In addition to Quaternary Aminoethyl (QAE-) Sephadex Chromatography (Negro Ponzi A, Cerio E, Angeretti A, et al; Comparison between five methods for the separation of IgM. Microbiologica 1983;6:121–132 and Sampson IA, Hodgen AN, Arthur IH: The separation of immunoglobulin M from human serum by fast protein liquid chromatography, J of Immunol Methods 1984;69:9–15), gel filtration (Ultrogel AcA34, BioGel A-5m) and anion exchange (DEAE-Sepharose CL-6B) were employed to prepare IgM from human serum. For the gel filtration, see Jehanli et al, (Jehanli H, Hough D; Rapid procedure for the isolation of human IgM myeloma proteins. J of Immunol Methods 1981;44:199–204). For the anion exchange, see Stephan W (Stephan W: Concentrated immunoglobulin solution suited for intravenous administration, U.S. Pat. No. 4,318,902, Mar. 9, 1982).

Cohn fraction III paste was the main virus contamination fraction. Following the AHF concentrate (FVIII) preparation with TNBP/Tween mixtures for virus inactivation (Horowitz B: Investigations into the application of tri(n-butyl) phosphate/detergent mixtures to blood derivatives; in Morgenthaler J-J (ed); Virus Inactivation in Plasma Products; No. 56 in Current Studies in Hematology and Blood Transfusion. Basel, Karger, 1989, pp.83–96), the IgM, IgG immunoglobulin concentrates prepared from Cohn fraction III was required for the virus inactivation step. The processes for the preparation of IgM, IgG immunoglobulin concentrates from Cohn Fraction III paste, virus inactivation with TNBP/Tween, and euglobulin precipitation with several low ionic strength buffer systems to remove TNBP/Tween have been demonstrated.

MATERIALS AND PREPARATION METHODS

Cohn fraction III paste prepared as a by-product from pooled normal plasma following methods of Cohn et al (Cohn E, Strong L, Hughes W, et al; Preparation and properties of serum plasma proteins. IV. A system for the separation into fractions of the protein and lipoprotein components of biological tissues and fluids, J Am Chem Soc 1946;68:459-675) and Oncley et al (Oncley J, Melin M, Richert D, et al; The separation of antibodies, isoagglutinins, prothrombin, plasminogen and beta-lipoprotein into subfractions of human plasma; J Am Chem Soc 1949;71:541-550) at Cutter Biological, Miles Inc., served as the source material for the enriched immunoglobulin M preparation. Octanoic acid (99% purity, mp. 16° C.) was obtained from Aldrich Chemical Company (Milwaukee, Wisconsin). All other chemical reagents are USP grade.

Isolation of Polyclonal IoM from Cohn Fraction III Paste

Cohn fraction III paste was suspended in 11-15 volumes of optimal low ionic strength acetate buffer, such as 0.05 M pH 3.5-4.0, and mixed at room temperature for 2-3 hours. The pH was adjusted to 4.68 with NaOH followed by the addition of 1.0-2.5% octanoic acid at room temperature mixed for 3-5 hours and left at 5° C. for several hours (NLT 8 hours), centrifuged at 5°-10° C., 10,800 xg forces for 45-60 minutes to precipitate out lipoproteins. Most immunoglobulins were in the caprylate supernatant.

Euglobulin Precipitation with Different Buffer Systems

The extract caprylate supernatant was passed through a prefilter, a sterile filter (0.2 u) and further ultrafiltered (UF)/diafiltered (DF) through a PM-30 membrane against a 7 volume exchange with WFI (water for injection) at 5°-15° C. until conductivity reached 0.03-0.06 mmho/cm and the pH was adjusted to 4.8 with acetic acid. The low ionic strength extract supernatant was further euglobulin precipitated with various buffer systems, such as tris buffer at pH 7.0-9.0 range and concentration at 0.005 M to 0.3 M; phosphate buffer at pH 6.5-8.0 and a concentration of 0.005 M to 0.01 M; imidazole buffer at pH 7.0-8.5 and a concentration of 0.0025 M to 0.0075 M; carbonate buffer at pH 9.5 and a concentration of 0.001 M to 0.01 M at room temperature or at 5° C. The euglobulin precipitant was further dissolved in 0.25 M glycine pH 4.25 or dissolved in water adjusted pH to 4.25 with acetic acid and further DF/UF against water. The concentration of IgM, IgG, and IgA was analyzed by radial immunodiffusion with quiplate system from Helena Laboratories (Beaumont, Texas) or by nephelometry assay with Behring IR Nephelometer from Behring Diagnostic Inc. (Somerville, N.J. . TNBP in the enriched IgM preparation was extracted with hexane and quantitatively determined by gas-liquid chromatography and tween-80 was determined by colorimetric method.

RESULTS

In order to remove virucidal agent for the plasma-derived IgM, IgG immunoglobulin concentrates preparation, the euglobulin precipitation process was introduced. The following tables were described to define the optimal condition for euglobulin precipitation process. The data in Table 1a indicated that the optimal condition of the tris-pH effect on IgM precipitation was 7.8 at both 5° C. and room temperature when employing 2% caprylate supernatant (3747-54) at low conductivity 0.05 MMHO/CM, pH 4.8, A280=0.01 M tris pH 7.8 resulted in final precipitation mixture at pH 7.2, conductivity 0.57 MMHO/CM and the composition being 49.9-56.1% IgM, 36.5-43% IgG and 7.2-7.4% IgA. Euglobulin precipitation at 5° C. resulted in a better yield (78.5%) than at room temperature (Table 1a). Table 1b showed that IgM was precipitated at the highest amount from caprylate supernatant (3747-54) with 0.01-0.015 tris pH 7.8 and the composition of the precipitant was 55.9-59.0% IgM, 34.2% IgG, 6.7-9.8% IgA. These results indicated that viricidal agent could be removed by euglobulin precipitation with 0.01 M tris pH 7.8 at 5° C. and resulted in highest amount of IgM in the tris precipitation fraction. The other buffer system such as phosphate buffer (0.005 M, pH 7.8) for euglobulin precipitation resulted in a lesser yield than with this buffer and as carbonate buffer (0.001 M, pH 9.5) resulted in a higher IgA content (Table 2). The optimal condition of imidazole buffer was 0.005 M, pH 7.8 for the globulin precipitation. Therefore, the two buffer systems such as tris buffer (0.01 M, pH 7.8) and imidazole buffer (0.005 M, pH 7.8) could be considered for euglobulin precipitation and employing imidazole buffer resulted in a better yield than with tris buffer (Table 2).

The following examples were carried out with caprylate supernatant after DF/UF at low conductivity (<0.06 MMHO/CM), pH 4.8 treated with 0.3% TNBP/1% Tween-80 followed euglobulin precipitation with tris or imidazole buffer.

TABLE 1a 0.01M Tris-pH effect on IgM Precipitation (5° C, and Room Temperature)

| Sample | Tris pH | IgM mg | Yield % | IgM | IgG (% of Total (IgM + IgG + IgA) | IgA |
|---|---|---|---|---|---|---|
| (3747-54) | 0 | 43.3 | | 11.1 | 79.4 | 9.5 |
| a. At R.T. 0.01M | 7.0 | 4.3 | 9.9 | 54.0 | 33.3 | 12.6 |
| | 7.2 | 7.6 | 17.6 | 53.7 | 34.5 | 11.9 |
| | 7.4 | 13.2 | 30.5 | 53.2 | 37.1 | 9.7 |
| | 7.6 | 20.8 | 48.0 | 54.0 | 38.7 | 7.3 |
| | 7.8 | 24.2 | 55.9 | 56.1 | 36.5 | 7.4 |
| | 8.0 | 19.6 | 45.3 | 51.0 | 41.1 | 7.8 |
| | 8.5 | 19.0 | 43.9 | 55.4 | 42.3 | 2.3 |
| | 9.0 | 12.0 | 27.7 | 58.9 | 38.3 | 2.8 |
| b. At 5° C. 0.01M | 7.0 | 6.72 | 15.5 | 55.3 | 28.9 | 15.8 |
| | 7.2 | 10.8 | 24.9 | 54.5 | 33.3 | 12.1 |
| | 7.4 | 10.4 | 24.0 | 36.7 | 48.0 | 15.4 |
| | 7.6 | 24.0 | 55.4 | 51.6 | 37.7 | 10.7 |
| | 7.8 | 34.0 | 78.5 | 49.9 | 43.0 | 7.2 |
| | 8.0 | 30.0 | 69.2 | 50.9 | 42.9 | 6.2 |

TABLE 1b

Tris-concentration Effect on IgM Precipitation

| Sample | Tris Conc. M | IgM Mg | IgM | IgG % of Total (IgM + IgG + IgA) | IgA |
|---|---|---|---|---|---|
| | 0.005 | 4.4 | 47.0 | 34.6 | 18.4 |
| | 0.01 | 13.2 | 55.9 | 34.2 | 9.8 |
| | 0.015 | 14.0 | 59.0 | 34.2 | 6.7 |
| | 0.02 | 11.8 | 55.5 | 38.2 | 6.4 |
| | 0.025 | 7.2 | 56.8 | 36.2 | 7.0 |
| | 0.03 | 6.2 | 54.8 | 39.1 | 6.0 |

TABLE 2

Study with Imidazole, Carbonate, Phosphate, Tris-buffer on IgM Precipitation (at room temperature).

| Sample | Tris pH 7.8 Conc. M | Phosphate pH 7.8 Conc. M | Carbonate pH 9.5 Conc. M | Imidazole 0.005M pH | Total IgM mg | IgM | IgG (% of Total IgM + IgG + IgA) | IgA |
|---|---|---|---|---|---|---|---|---|
| 16102-43 (3747-54) 2% Caprylate Supernatant | — | — | — | — | 17.4 | 13.9 | 75.0 | 7.2 |
| a. Tris pH pH 7.8 | 0.01 | — | — | — | 7.10 | 55.8 | 37.3 | 6.9 |
|  | 0.02 | — | — | — | 5.15 | 62.3 | 33.9 | 3.9 |
| b. Phosphate pH 7.8 | — | 0.005 | — | — | 6.50 | 58.1 | 36.0 | 5.8 |
|  | — | 0.01 | — | — | 2.50 | 68.5 | 27.1 | 4.4 |
| c. Carbonate pH 9.5 | — | — | 0.001 | — | 8.25 | 38.0 | 47.5 | 14.5 |
|  | — | — | 0.005 | — | 6.60 | 45.7 | 40.1 | 14.2 |
|  | — | — | 0.007 | — | 8.97 | 47.2 | 42.8 | 10.0 |
|  | — | — | 0.01 | — | 7.13 | 53.8 | 40.3 | 6.0 |
| d. Imidazole 0.005M | — | — | — | 8.5 | 12.75 | 44.4 | 45.6 | 10.0 |
|  | — | — | — | 8.0 | 10.42 | 37.5 | 53.3 | 9.2 |
|  | — | — | — | 7.8 | 10.18 | 46.4 | 42.6 | 10.9 |
|  | — | — | — | 7.6 | 10.50 | 46.0 | 42.1 | 11.8 |
|  | — | — | — | 7.4 | 11.12 | 50.8 | 38.4 | 11.0 |
|  | — | — | — | 7.2 | 8.1 | 50.5 | 36.8 | 12.8 |
|  | — | — | — | 7.0 | 6.1 | 50.5 | 35.6 | 13.9 |

EXAMPLE 1

Euglobulin precipitation with 0.01 M Tris pH 7.8 at room temperature or at 5° C. resulted in a 43-67% yield, containing 1.9-2.7 μg of TNBP/mg IgM (99.9% TNBP removed) and 50-70% IgM, 30-50% IgG, 2-10% IgA in the precipitant mixture (Table The results in Table 3 also indicate that euglobulin precipitation with 0.005 M imidazole pH 7.8 at room temperature or at 5° C. gave similar TNBP/Tween 80 content (99.9% TNBP/Tween removal), higher yield (84.3%) at 5° C. process and 37.2% IgM, 51.9% IgG, 10.9% IgA in the precipitant mixture.

precipitation with 0.01 M tris buffer pH 7.8 at C (Step 2) resulted in conductivity 0.45-0.60 MMHO/CM, pH 6.0-7.5 and 54.3%-67.1% IgM, 23.2%-38.8% IgG and 4.6-10.1% IgA in the final precipitant mixture. The precipitate was further washed with $1 \times 10^4$ M tris pH 7.8 to remove trace amount of TWBP/Tween-80. The precipitate suspended in water pH 4.25 and diafiltered against WFI resulted in less than 0.4 μg TNBP/Tween-80 per mg IgM in the final IgM, IgG immunoglobulin concentrate preparation (Table 4).

TABLE 4

Euglobulin Precipitation with Tris Buffer

TABLE 3

Study TNBP/Tween Treatment at Caprylate Supernatant DF/UF

| Sample | IgM mg/ml | Yield IgM % | IgM | IgG (% of Total (IgM + IgG + IgA) | IgA | Tween-80 ug/mg IgM | TNBP ug/mg IgM |
|---|---|---|---|---|---|---|---|
| 1. 16168-69-1 (2% Cap. Sup. DF/UF pH 4.8 + TNBP/Tween) | 1.06 | 100 | 19.2 | 74.3 | 6.5 | 8,100 | 2,462 |
| 16168-71-1B (Tris ppt. at R.T.) | 5.46 | 43.1 | 71.7 | 25.9 | 2.4 | 2.7 | <0.18 |
| 16168-71-2B (Tris ppt. at 5° C.) | 8.32 | 67.2 | 63.8 | 33.2 | 3.1 | 2.2 | <0.19 |
| 2. 16168-69-2 (2% Cap. Sup. DF/UF (16135-84-3B) pH 4.8 + TNBP/Tween) | 1.69 | 100 | 13.8 | 79.8 | 6.4 | 4,461 | 1,337 |
| 16168-71-3B (Tris ppt at R.T.) | 11.64 | 57.3 | 56.1 | 45.2 | 5.8 | 1.9 | 0.8 |
| 16168-71-4B (Tris ppt at 5° C.) | 11.54 | 57.3 | 44.9 | 48.4 | 4.3 | 2.6 | 2.2 |
| 16168-71-5B (Imidazole ppt at RT) | 10.03 | 50.8 | 38.0 | 51.3 | 10.7 | 2.4 | 1.1 |
| 16168-71-6B (Imidazole ppt at 5° C.) | 16.32 | 84.3 | 37.2 | 51.9 | 10.9 | 1.6 | 0.6 |

EXAMPLE 2

In the scale-up process, 4 lots of plasma-derived IgM, IgG immunoglobulin concentrate prepared from 15 Kg, 135 Kg Cohn fraction III paste, 2% caprylate supernatant after DF/UF at low conductivity 0.11-0.20 MMHO/CM, pH 4.76 to 4.85, A280=34.8-40.0 treated with 0.3% TNBP, 1% Tween-80 at 24.C NLT (not less than) 8 hours for virus inactivation (Step 1), the whole mixture was diluted with WFI to result conductivity at 0.03-0.06 MMHO/CM (Table 4). Following euglobulin

| Lot # | 3463-24 | 18189-1-I | 18189-32-H | 9094-21-J |
|---|---|---|---|---|
| FIII (Kg) | (135) | (15) | (15) | (15) |
| Step 1 Virus Inactivation (Caprylate Sup. + TNBP/Tween) | | | | |
| A280 | 34.8 | 37.1 | 36.9 | 39.6 |
| Conductivity (MMHO/CM) | 0.18 | 0.13 | 0.11 | 0.16 |
| pH | 4.77 | 4.85 | 4.80 | 4.80 |
| Dilution c WFI | | | | |

TABLE 4-continued

Euglobulin Precipitation with Tris Buffer

| Lot #<br>FIII (Kg) | 3463-24<br>(135) | 18189-1-I<br>(15) | 18189-32-H<br>(15) | 9094-21-J<br>(15) |
|---|---|---|---|---|
| A280 | 11.1 | 11.42 | 11.25 | 8.1 |
| Conductivity (MMHO/CM) | 0.06 | 0.03 | 0.03 | 0.04 |
| Step 2 Euglobulin Precipitation c 0.01M Tris pH 7.8 | | | | |
| Conductivity (MMHO/CM) | 0.45 | 0.57 | 0.59 | 0.46 |
| pH | 6.8 | 7.26 | 6.70 | 6.38 |
| Precipitant | | | | |
| % IgM | 54.3 | 58.3 | 56.2 | 67.1 |
| % IgG | 38.8 | 37.1 | 33.7 | 23.2 |
| % IgA | 6.9 | 4.6 | 10.1 | 9.6 |
| TNBP (μg/mg IgM) | <0.04 | <0.03 | <0.03 | <0.03 |
| Tween-80 (μg/mg IgM) | 0.35 | <0.3 | 0.16 | 0.4 |

EXAMPLE 3

Plasma-derived IgM, IgG immunoglobulin concentrates prepared from 15 kg Cohn fraction III paste, 2% caprylate supernatant after DF/UF at pH 4.8, treated with TNBP/Tween-80, followed euglobulin precipitation with 0.1–0.2 M NaOH, adjusted pH to 6.0–7.0, resulted in 0.4 μg TWBP/Tween-80 per mg IgM and 33.5–45.9% IgM, 40.2–56% IgG, 10.4–13.8% IgA in the final IgM, IgG immunoglobulin concentrates (Table 5).

TABLE 5

| Lot # | 9094-20K | 9094-50-2 |
|---|---|---|
| Step 1 Virus Inactivation (Cap. Sup. + TNBP/Tween) | | |
| A280 | 37.44 | 32.0 |
| Conductivity (MMHO/CM) | 0.15 | 0.13 |
| pH | 4.76 | 4.81 |
| Dilution c WFI | | |
| A280 | 8.00 | 10.44 |
| Conductivity (MMHO/CM) | 0.03 | 0.04 |
| Step 2 Euglobulin Precipitation cNaOH | | |
| Conductivity (MMHO/CM) | 0.12 | 0.11 |
| pH | 6.98 | 6.3 |
| Precipitant | | |
| % IgM | 33.5 | 45.9 |
| % IgG | 56.0 | 40.2 |
| % IgA | 10.4 | 13.8 |
| TNBP (μg/mg IgM) | 0.4 | 0.3 |
| Tween | 0.4 | 0.5 |

The preceding examples illustrate the principle features of the present invention that the pH, conductivity and antibody concentration of the solution are changed under conditions sufficient to assure the precipitation of substantially all antibodies and maintaining substantially all of the virucidal agent in the supernatant solution.

DISCUSSION

This study showed that the IgM IgG immunoglobulin concentrates isolated from Cohn fraction III paste and freed lipid, prekallikrein activator (PKA) by treatment with at least 1% caprylate acid was followed by euglobulin precipitation with a different buffer system. The pH, concentration, kind of buffer, and temperature affected IgM, IgG, and IgA precipitation from isolated caprylate supernatant. Euglobulin precipitation at 5° C. with all kinds of buffers resulted in a higher yield of IgM preparation than at 20°–22° C. The lower ionic strength (conductivity) buffers such as imidazole (0.005M) by euglobulin precipitation gave the highest yield of IgM but also contained higher IgA than those with tris buffer. Previously, IgM was prepared by euglobulin precipitation with extract supernatant being dialyzed against 0.001 M phosphate buffer pH 6.5, see Van Der Hoven A, Conradie JD, Bubb M: The isolation of immunogenically pure IgM from Cohn fraction III of pooled normal human plasma. Immunochemistry 1973;10:107–114. However, our studies for euglobulin precipitation with phosphate buffer (0.005 M, pH 7.8) resulted in less yield than that with tris buffer. And the IgM precipitation with phosphate buffer gave aggregate generation and higher anticomplement activity by C4a RIA assay. With the carbonate buffer having the narrow pH range such as 9.5 resulted in a high IgA content. Therefore, the best buffer system for euglobulin precipitating was with tris buffer (0.01 M, pH 7.8) at 5° C.

The conductivity and pH of caprylate supernatant also affected the euglobulin precipitation with various buffer systems. The lowest conductivity (<0.05 mmho/cm) and optimal pH 4.8–5.1 of caprylate supernatant resulted in the highest IgM precipitation with tris buffer. Enriched IgM preparation for clinical use isolated from virus enriched Cohn fraction III was required for virus inactivation with TNBP/Tween treatment adopted from the New York Blood Center's licensed method, see Horowitz B: Investigations into the application of tri (n-butyl)phosphate/detergent mixtures to blood derivatives; in Morgenthaler J-J (ed): Virus Inactivation in Plasma Products; No. 56 in Current Studies in Hematology and Blood Transfusion. Basel, Karger, 1989, pp.83–96.

If caprylate supernatant in imidazole buffer pH 7.0 was virus inactivated with TNBP/Tween, the salt and TNBP/Tween removal created problems during the purification process. TNBP can cause diafiltration membrane system damage and Tween with protein solution formed miscellanea that could not be removed by the diafiltration system. However, caprylate supernatant after DF/UF resulted in low conductivity (<0.05 mmho/cm) at pH 4.8 without buffer in the presence of TNBP/Tween which had virucidal activity. And TNBP/Tween was removed by euglobulin precipitation with tris/imidazole buffer and most of the TNBP/Tween were present in the supernatant. The enriched IgM preparation after TNBP/Tween treatment gave a reasonable yield, trace amount of TNBP/Tween, and retained their biological activity for human clinical use.

Given the above disclosure, it is thought that variations will occur to those skilled in the art. Accordingly, it is intended that the above examples should be construed as illustrative only and that the scope of the invention disclosed here should be limited only by the following claims.

I claim:

1. A method of preparing an antibody preparation comprising both IgM and IgG antibodies, the method comprising the steps of (a) mixing a source for the IgM and IgG antibodies in an aqueous solution in the presence of tri-n-butyl phosphate, the solution having a conductivity ranging from about 0.03 to 0.20 M MHO/CM, a pH ranging from about 4.75 to 4.85 and a protein concentration when measured at A280 ranging from about 5 to 40, to assure inactivation of substantially all viruses present; and (b) subjecting the solution to conditions sufficient to precipitate substantially all of the antibodies from the solution while maintaining substantially all of the tri-n-butyl phosphate in the supernate by simultaneously assuring a solution conductivity ranging from about 0.05 to 0.70 M MHO/CM, a pH ranging from about 6.0 to 7.5 and an amount of IgM antibody proportion in the precipitate ranging from about 20 to 80% by weight total protein precipitate.

2. The method of claim 1 wherein the source for the antibodies in Cohn Fraction III paste.

3. The method of claim 1 wherein the tri-n-butyl phosphate is water soluble at a pH ranging from about 4.75 to 7.5.

4. The method of claim 1 wherein at least 10% by weight of the source antibodies are precipitated in step (b) and at least 99% by weight of the original tri-n-butyl phosphate remains in the supernate.

5. The method of claim 1 wherein the IgM antibodies precipitated in step (b) are at least 40% by weight of the total IgM antibodies in the source antibodies and at least 99.9% by weight of the original tri-n-butyl phosphate remains in the supernatant.

6. The method of claim 4 wherein the IgM antibody comprises at least about 30% by weight of the total antibody in the precipitate.

7. The method of claim 6 wherein the virucidal agent comprises Tween-80.

* * * * *

UNITED STATES PATENT AND TRADEMARK OFFICE
CERTIFICATE OF CORRECTION

PATENT NO. : 5,110,910
DATED : May 5, 1992
INVENTOR(S) : Grace C. Tsay

It is certified that error appears in the above-identified patent and that said Letters Patent is hereby corrected as shown below:

On Title page, item [75], "Grace C. Tsav, should read as follows:

--Grace C. Tsay--.

Signed and Sealed this

Twenty-second Day of June, 1993

Attest:

MICHAEL K. KIRK

*Attesting Officer*     Acting Commissioner of Patents and Trademarks